US011408856B2

(12) United States Patent
Abdelhamid

(10) Patent No.: US 11,408,856 B2
(45) Date of Patent: Aug. 9, 2022

(54) SYSTEMS AND METHODS FOR MONITORING HEALTH OF CORE SAMPLES

(71) Applicant: Saudi Arabian Oil Company, Dhahran (SA)

(72) Inventor: Osama Abdelgawad Ahmed Abdelhamid, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 287 days.

(21) Appl. No.: 16/733,885

(22) Filed: Jan. 3, 2020

(65) Prior Publication Data
US 2021/0208105 A1 Jul. 8, 2021

(51) Int. Cl.
G01N 29/04 (2006.01)
H04N 5/225 (2006.01)

(52) U.S. Cl.
CPC ........... *G01N 29/04* (2013.01); *H04N 5/2251* (2013.01); *G01N 2291/023* (2013.01)

(58) Field of Classification Search
CPC ........................ E21B 25/005; G01N 2291/023; G01N 29/04; G01N 33/24; H04N 5/2251
See application file for complete search history.

(56) References Cited

U.S. PATENT DOCUMENTS

| 6,876,721 | B2 | 5/2005 | Siddiqui |
| 8,146,684 | B2 | 4/2012 | Cravatte |
| 8,162,080 | B2 | 4/2012 | Castillo |
| 9,399,900 | B2 | 7/2016 | Hoeink et al. |
| 10,066,455 | B2 | 9/2018 | Hejleh et al. |

(Continued)

FOREIGN PATENT DOCUMENTS

| CA | 3034082 A1 | * | 8/2019 | |
| CN | 205931655 U | | 2/2017 | |
| CN | 109155064 A | * | 1/2019 | ............ E21B 49/02 |

(Continued)

OTHER PUBLICATIONS

English machine translation of Kleyn et al. (CA-3034082-A1) (Year: 2019).*

(Continued)

*Primary Examiner* — Roy Y Yi
*Assistant Examiner* — Geoffrey T Evans
(74) *Attorney, Agent, or Firm* — Bracewell LLP; Constance G. Rhebergen; Linda L. Morgan

(57) ABSTRACT

Methods, systems, and apparatuses for monitoring health and integrity of core samples are disclosed. The apparatus includes a core container including a body portion having a plurality of chambers to accommodate a plurality of samples, and a lid portion configured to fully cover the body portion, and one or more vibration sensing devices configured to measure vibration experienced by each of the plurality of core samples. The apparatus is further configured to access a database comprising a plurality of core rock matrices and corresponding threshold vibration amplitude values, and determine, for each of the core samples, a category from a plurality of categories based on the vibration experienced by the core sample and the threshold vibration amplitude value for the corresponding core rock matrix.

18 Claims, 4 Drawing Sheets

(56) References Cited

U.S. PATENT DOCUMENTS

2010/0000108 A1  1/2010  Stockton
2018/0039900 A1  2/2018  Hoeink et al.

FOREIGN PATENT DOCUMENTS

RU      2627773 C2    8/2017
WO   2011082563 A1    7/2011

OTHER PUBLICATIONS

English machine translation of Mezghani et al. (CN-109155064-A) (Year: 2019).*
Baker Hughes; "CoreCare Sservices Surface Handling, processing, and transportation" 2019; available as of May 5, 2021 at: https://www.bakerhughes.com/sites/bakerhughes/files/2020-08/CoreCare-services-broc_FINAL%20VERSION.pdf; pp. 1-5.
Garcia, Jean-Valery et al.; "Well Site Core Stabilization and Packaging—the First Step in Acquiring Undisturbed Core." International Symposium of the Society of Core Analysts, Halifax, Nova Scotia, Oct. 4-7, 2010; pp. 1-6.
Hartwig, Troy; Evaluation of Transportation Vibration Associated with Relocation of Work in Process as Part of KCRIMS: KCP-613-9161 Final Report Federal Manufacturing & Technologies, Apr. 2013; pp. 1-48.
International Search Report and Written Opinion for International Application No. PCT/US2020/067681 report mail dated Apr. 15, 2021; pp. 1-12.
Paternoster, A. et al.; "Measurement and analysis of vibration and shock levels for truck transport in Belgium with respect to packaged beer during transport" Food Packaging and Shelf Life, vol. 15, Mar. 1018; pp. 134-143.

* cited by examiner

SYSTEMS AND METHODS FOR MONITORING HEALTH OF CORE SAMPLES

BACKGROUND

1. Technical Field

Embodiments generally relate to systems and methods for monitoring the health of core samples obtained from a subsurface formation.

2. Description of the Related Art

Core analysis plays an important role in the oil and gas industry. Retrieval and lab analysis of core samples is essential for reservoir management during every phase in the life cycle of all oil and gas fields. Lab analysis of core samples provides a suite of rock and fluid properties that are crucial for evaluating reservoir performance, and thus enable the engineers to make better reservoir management decisions to enhance the ultimate recovery of the reservoir. Properly analyzed core samples provide valuable insight into the reservoir, which is difficult to obtain from other sources. Core samples are essential to understanding the nature of the pore system in the potential reservoir unit, and consequently, core samples provide direct evidence of the presence and quantity of hydrocarbons in the reservoir and even more importantly, yield valuable insight into the design of the best deliverability mechanism of the oil and gas, thus enhance the ultimate reserves.

SUMMARY

A common misconception in the coring industry is that a coring job is complete once a good quality core is brought to the surface at the rig location. Surely, this is an important step in the coring process, but it is certainly not the last. In fact, it just forms the first step of a reliable and a valid core lab testing process. A core sample can easily be damaged and be rendered useless during its transport from the rig surface to the core lab where the sample will undergo various core tests, or while handling the core either at the rig location or at the lab. This is especially true in the case of a soft and/or a brittle core sample, where the chances of core damage is more likely. Thus, proper core handling is critical in the core acquisition process and all the core-handling tasks should be carried out without affecting the core health and integrity.

Currently, core handling tasks at the rig surface and the journey of the core from the rig surface to the core lab is not fully monitored and tracked. If the core sample is found to have been crushed or having lost its physical integrity, then the core lab results may not be credible, and may be even considered invalid.

Accordingly, an object of the present disclosure is to introduce better accountability and vigilance onto the core transport and core-handling processes by recording and flagging mechanical vibrations and shocks that may affect the physical integrity of the core sample before the core sample undergoes lab analysis.

One example embodiment is an apparatus for monitoring and registering shocks and vibrations that may affect the mechanical health and the physical integrity of the core sample. The apparatus may be used to track the mechanical health of the core during core transport and various core-handling tasks, by measuring and logging pulses, vibrations, and shocks that may affect the mechanical health and physical integrity of the core sample. The apparatus can be configured to alert the user with a sound alarm in real time when the device records vibrations beyond a threshold vibration amplitude (TVA), a level of vibration at which the core is determined to start to lose its mechanical integrity. This TVA value is a function of the geomechanical properties of the rock matrix. The apparatus can also be configured with a database of TVA values of the most common core rock matrices so as to make the apparatus more user-friendly.

In one embodiment, as soon as a healthy core sample is obtained by the rig, the healthy core sample is carefully placed in the vibration tracking apparatus. In order to maintain the mechanical health and physical integrity of the core sample, the apparatus tracks mechanical vibrations along the core transport and core handling processes, and in case the vibration reaches close to the TVA value, an alarm sound alerts the user handling the core. In one embodiment, the apparatus may indicate the calculated mechanical health of the core sample at the time of its lab test in a color regimented scheme, for example, a green color would indicate a mechanically healthy code, orange color would indicate a partially damaged core, and red color would indicate a damaged core sample. As a result, the apparatus increases the confidence in reservoir insights derived from core sampling, and enhancing the credibility and reliability of the core sampling results.

In one embodiment, the apparatus may also include an imaging device, such as a camera or a high definition video camera to provide pictures and videos of the core samples contained inside the apparatus. The data from the apparatus can be communicated on a real time basis to a computer which controls the core operations process and display pictures or live videos of the core environment during the core handling process on the surface and during core transportation to the lab. In one embodiment, the apparatus may include a shock absorber to eliminate or damp sudden shock, vibrations, and impulses.

BRIEF DESCRIPTION OF THE DRAWINGS

All aspects and features of certain example embodiments of the present disclosure will be more apparent from the following description taken in conjunction with the accompanying drawings, in which.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Details of one or more implementations are set forth in the accompanying drawings and in the description below. Further embodiments, features, and aspects will become apparent from the description, the drawings, and the claims. Embodiments set forth in the claims encompass all available equivalents of those claims.

Figure 1:
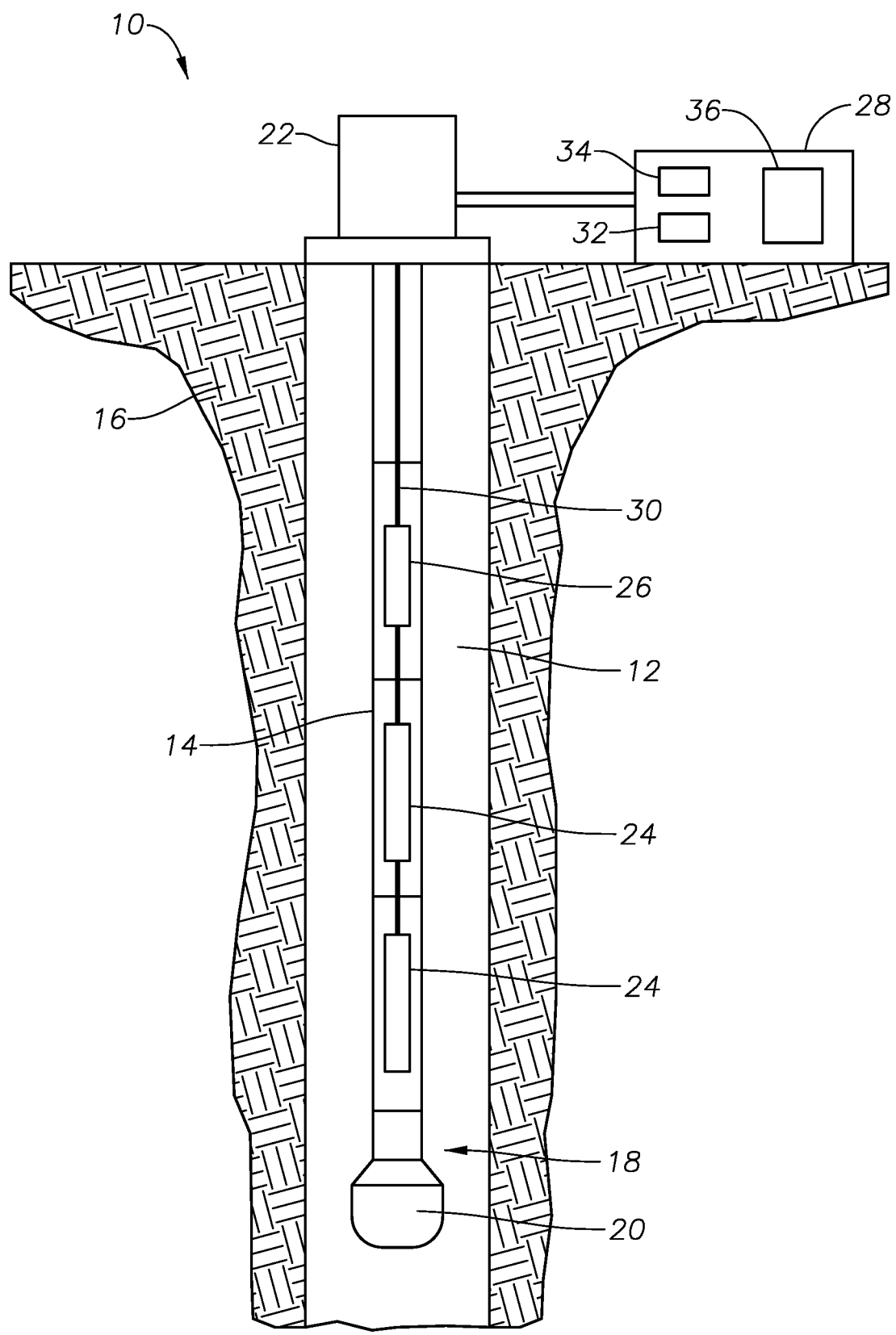
FIG. 1 illustrates a system for obtaining a core sample from a subsurface formation, according to one or more example embodiments.

The systems and methods described herein provide for a method for monitoring the health and integrity of core samples obtained from a subsurface formation. Referring to FIG. 1, an exemplary embodiment of a downhole drilling system 10 disposed in a borehole 12 is shown. A drill string 14 is disposed in the borehole 12, which penetrates at least one earth formation 16. Although the borehole 12 is shown in FIG. 1 to be of constant diameter, the borehole is not so limited. For example, the borehole 12 may be of varying diameter and/or direction (e.g., azimuth and inclination). The drill string 14 is made from, for example, a pipe or multiple pipe sections. The system 10 and/or the drill string 14 include a drilling assembly 18. In one embodiment, the drilling assembly is configured as a coring assembly or tool. Various measurement tools may also be incorporated into the system 10 to affect measurement regimes such as wireline measurement applications or logging-while-drilling (LWD) applications.

The drilling assembly 18, which may be configured as a bottomhole assembly (BHA), includes a drill bit 20 and is configured to be conveyed into the borehole 12 from a drilling rig 22. In one embodiment, the drilling assembly is a coring assembly configured to obtain core samples of the formation 16. The drill bit 20 in this embodiment is a coring bit incorporated as part of a coring or sampling tool. An exemplary tool includes a coring bit attached to a drill collar having an inner bore configured to receive and retain the core sample.

In one embodiment, one or more downhole components, such as the drill string 14 and the drilling assembly 18, include sensor devices 24 configured to measure various parameters of the formation and/or borehole. For example, one or more parameter sensors (or sensor assemblies such as LWD subs) are configured for formation evaluation measurements relating to the formation, borehole, geophysical characteristics and/or borehole fluids. These sensors may include formation evaluation sensors (e.g., resistivity, dielectric constant, water saturation, porosity, density and permeability), sensors for measuring geophysical parameters (e.g., acoustic velocity and acoustic travel time), and sensors for measuring borehole fluid parameters (e.g., viscosity, density, clarity, rheology, pH level, and gas, oil and water contents).

The sensor devices 24, drilling assembly 18 and other downhole components may be included in or embodied as a BHA, drill string component or other suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tubing type, of the jointed pipe type and any combination or portion thereof. Other carrier examples include casing pipes, wirelines, wireline sondes, slickline sondes, drop shots, downhole subs, bottom-hole assemblies, and drill strings.

In one embodiment, the drilling assembly 18 and sensor devices 24 are configured to communicate with one or more processors, such as a downhole electronics unit 26 and/or a surface processing unit 28. The processor(s) may receive data and communication signals from the downhole components and/or transmit control signals to the components. Signals and data may be transmitted via any suitable transmission device or system, such as a cable 30. Other techniques used to transmit signals and data include wired pipe, electric and/or fiber optic connections, mud pulse, electromagnetic and acoustic telemetry.

The processor or processors, in one embodiment, are configured to receive data and generate information such as a mathematical model for prediction of downhole parameters and conditions. For example, the processor is configured to receive downhole data as well as additional data (e.g., from a user or database) such as geometric data of borehole components. The processor may be configured to perform functions such as providing prediction or modeling information, controlling the drilling assembly 18, transmitting and receiving data and monitoring the drilling assembly 18 and the drill string 14. The surface processing unit 28, the sensor devices 24 and/or other components may also include components as necessary to provide for storing and/or processing data collected from various sensors therein. For example, the surface processing unit 28 includes a processor 32, a data storage device (or a computer-readable medium) 34 for storing, data, models and/or computer programs or software 36.

Although the processors described herein are shown in communication with downhole components, they are not so limited. For example, a processor can be embodied as an independent computer or other processing device that can receive input data such as model parameters, measurement information and proposed tripping schedules.

Generally, some of the teachings herein are reduced to an algorithm that is stored on machine-readable media. The algorithm is implemented by a computer or processor such as the surface processing unit 28 and provides operators with desired output.

Figure 2:
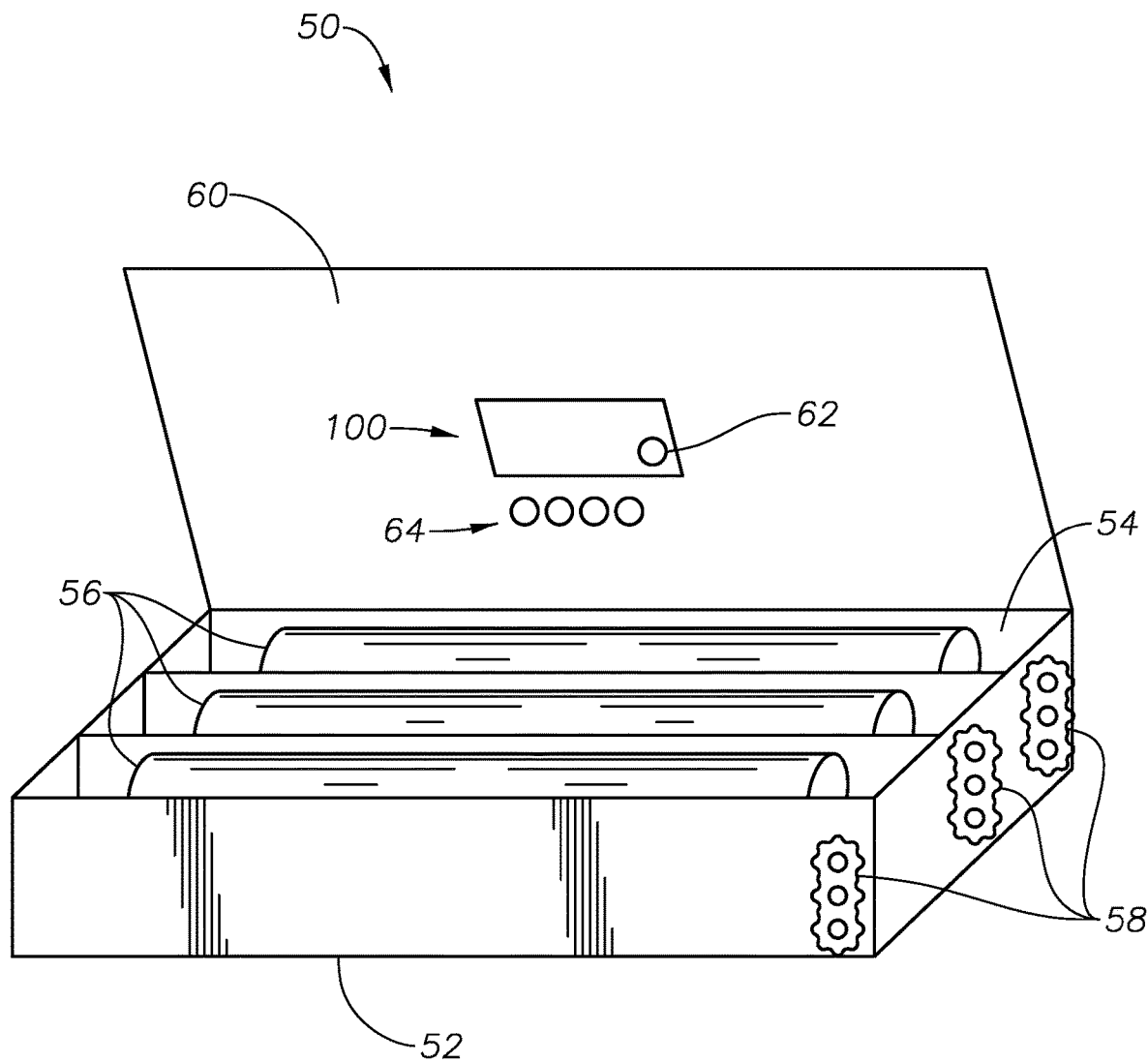
FIG. 2 illustrates an apparatus for monitoring health and integrity of a core sample, according to one or more example embodiments.

After a plurality of core samples of the subsurface formation are obtained, the core samples may be placed in an apparatus for transportation to the lab where further core testing may be conducted. FIG. 2 illustrates an example apparatus 50 for monitoring health and integrity of core samples 56 obtained from a subsurface formation, according to one or more example embodiments. The apparatus 50 may include a core container with a body portion 52 having a plurality of chambers 54 to accommodate a plurality of samples 56. The core container may also include a lid portion 60 configured to fully cover the body portion 52. The apparatus 50 may also include one or more vibration sensing devices 100 configured to measure vibration experienced by each of the plurality of core samples 56. Although the vibration sensing device 100 is illustrated to be installed on the lid portion 60 of the apparatus 50, the disclosure is not so limited. For example, a vibration sensing device 100 may be installed individually in connection with each of the core samples, in or around each of the chambers 54. The vibration sensing device 100 may include an accelerometer 62 configured to measure vibration experienced by the respective core sample.

An accelerometer is a device that measures proper acceleration. Proper acceleration, being the acceleration (or rate of change of velocity) of a body in its own instantaneous rest frame, is not the same as coordinate acceleration, being the acceleration in a fixed coordinate system. For example, an accelerometer at rest on the surface of the Earth will measure an acceleration due to Earth's gravity, straight upwards of $g \approx 9.81$ m/s$^2$. By contrast, accelerometers in free fall (falling toward the center of the Earth at a rate of about 9.81 m/s$^2$) will measure zero.

In one embodiment, the apparatus 50 may include single or multi-axis models of accelerometers to detect magnitude and direction of the proper acceleration, as a vector quantity, and can be used to sense orientation (because direction of weight changes), coordinate acceleration, vibration, shock, and falling in a resistive medium (a case where the proper acceleration changes, since it starts at zero, then increases). Micromachined microelectromechanical systems (MEMS) accelerometers can also be used to detect the position of the core samples.

The vibration sensing device 100 may also include a three-axis gyro (not-shown) configured to measure rotation of the core samples around three axes: x, y, and z. A gyroscope is a device used for measuring orientation and angular velocity of the core samples. It is a spinning wheel or disc in which the axis of rotation (spin axis) is free to assume any orientation by itself. When rotating, the orientation of this axis is unaffected by tilting or rotation of the mounting, according to the conservation of angular momentum.

Gyroscopes based on other operating principles also exist, such as the microchip-packaged MEMS gyroscopes found in electronic devices, solid-state ring lasers, fibre optic gyroscopes, and the extremely sensitive quantum gyroscope, which may also be used in apparatus 50.

In one embodiment, the apparatus 50 may also include one or more high definition cameras 64 configured to capture images and/or videos of the one or more core samples. The apparatus 50 may further include a wireless transmitter (shown in further detail in FIG. 3) configured to transmit the vibration data, image data, or video data to a receiver. The wireless transmitter may be wirelessly connected to the receiver via radio frequency, Bluetooth, Bluetooth low energy, ZigBee, Wi-Fi, 2G, 3G, 4G LTE, 5G, or other wireless communication technique. In one embodiment, the apparatus 50 may also include a battery unit configured to provide power to the one or more vibration sensing devices 100, the one or more high definition cameras 64, and the wireless transmitter.

One example embodiment is an apparatus 50 for monitoring and registering shocks and vibrations that may affect the mechanical health and the physical integrity of the core sample 56. The apparatus 50 may be used to track the mechanical health of the core sample 56 during core transport and various core-handling tasks, by measuring and logging pulses, vibrations, and shocks that may affect the mechanical health and physical integrity of the core sample 56. The apparatus 50 can be configured to alert the user with a sound alarm in real time when the device records vibrations beyond a threshold vibration amplitude (TVA), a level of vibration at which the core is determined to start to lose its mechanical integrity. This TVA value is a function of the geomechanical properties of the rock matrix. The apparatus can also be configured with access to a database of TVA values of the most common core rock matrices so as to make the apparatus 50 more user-friendly.

In one embodiment, as soon as a healthy core sample is obtained by the rig, the healthy core sample is carefully placed in the vibration tracking apparatus 50. In order to maintain the mechanical health and physical integrity of the core sample, the apparatus 50 tracks mechanical vibrations along the core transport and core handling processes, and in case the vibration reaches close to the TVA value, an alarm sound alerts the user handling the core. In one embodiment, the apparatus may indicate the calculated mechanical health of the core sample at the time of its lab test in a color regimented scheme, for example, a green color would indicate a mechanically healthy code, orange color would indicate a partially damaged core, and red color would indicate a damaged core sample. As a result, the apparatus increases the confidence in reservoir insights derived from core sampling, and enhancing the credibility and reliability of the core sampling results.

In one embodiment, the apparatus may also include an imaging device, such as a camera or a high definition video camera to provide pictures and videos of the core samples contained inside the apparatus. The data from the apparatus can be communicated on a real time basis to a computer which controls the core operations process and display pictures or live videos of the core environment during the core handling process on the surface and during core transportation to the lab. In one embodiment, the apparatus may include a shock absorber to eliminate or damp sudden shock, vibrations, and impulses.

The apparatus 50 may also include one or more processors, and a computer readable medium including computer readable instructions that when executed by the processor cause the processor to access a database including a plurality of core rock matrices and corresponding threshold vibration amplitude values. The processors may also be configured to, by way of computer executable code, to determine, for each of the core samples, a category from a plurality of categories based on the vibration experienced by the core sample and the threshold vibration amplitude value for the corresponding core rock matrix. The database may be stored locally on the computer readable medium or remotely on a computer or server.

As indicated above, the apparatus may indicate the calculated mechanical health of the core sample at the time of its lab test in a color regimented scheme, for example, a green color would indicate a mechanically healthy code, orange color would indicate a partially damaged core, and red color would indicate a damaged core sample. As a result, the apparatus increases the confidence in reservoir insights derived from core sampling, and enhancing the credibility and reliability of the core sampling results.

In one embodiment, the apparatus 50 may also include a plurality of shock dampening devices 58 configured to reduce an amount of shock experienced by each of the core samples 56.

Figure 3:
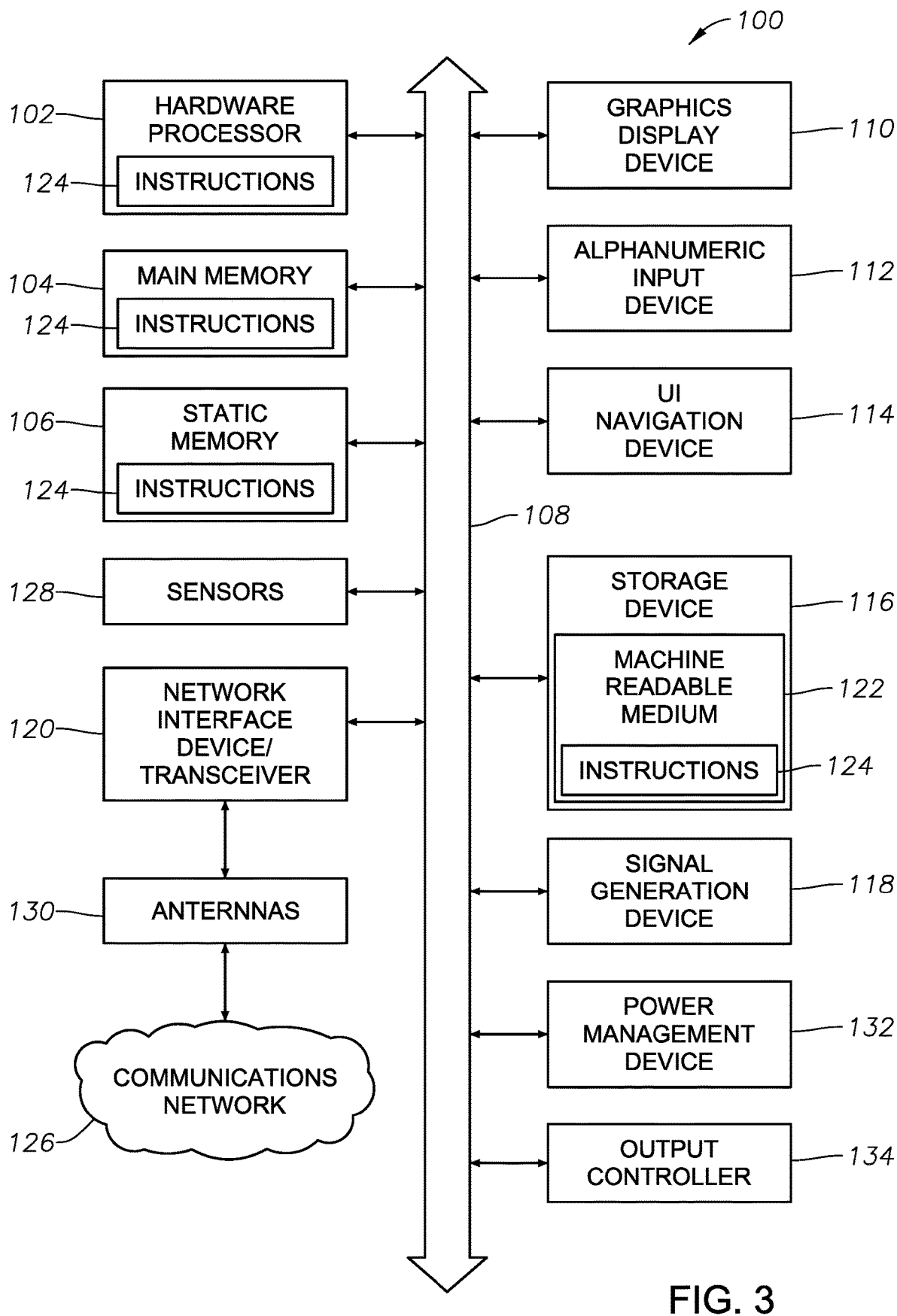
FIG. 3 illustrates a device within the apparatus of FIG. 2, according to one or more example embodiments.

FIG. 3 illustrates in further detail an example vibration sensing device 100, according to one or more example embodiments of the present disclosure. The device 100 may operate as a standalone device or may be connected (e.g., networked) to other machines.

The device (e.g., computer system) 100 may include a hardware processor 102 (e.g., a central processing unit (CPU), a graphics processing unit (GPU), a hardware processor core, or any combination thereof), a main memory 104 and a static memory 106, some or all of which may communicate with each other via an interlink (e.g., bus) 108. The device 100 may further include a power management device 132, a graphics display device 110, an alphanumeric input device 112 (e.g., a keyboard), and a user interface (UI) navigation device 114 (e.g., a mouse). In an example, the graphics display device 110, alphanumeric input device 112 and UI navigation device 114 may be a touch screen display. The device 100 may additionally include a storage device (i.e., drive unit) 116, a signal generation device 118 (e.g., a speaker), a network interface device/transceiver 120 coupled to antenna(s) 130, and one or more sensors 128, such as a global positioning system (GPS) sensor, compass, accelerometer, or other sensor. The device 100 may include an output controller 134, such as a serial (e.g., universal serial bus (USB), parallel, or other wired or wireless (e.g., infrared (IR), near field communication (NFC), etc.) connection to communicate with or control one or more peripheral devices (e.g., a printer, card reader, etc.).

The storage device 116 may include a machine readable medium 122 on which is stored one or more sets of data structures or instructions 124 (e.g., software) embodying or utilized by any one or more of the techniques or functions described herein. The instructions 124 may also reside, completely or at least partially, within the main memory 104, within the static memory 106, or within the hardware processor 102 during execution thereof by the device 100. In an example, one or any combination of the hardware processor 102, the main memory 104, the static memory 106, or the storage device 116 may constitute machine readable media.

While the machine readable medium 122 is illustrated as a single medium, the term "machine readable medium" may include a single medium or multiple media (e.g., a centralized or distributed database, and/or associated caches and servers) configured to store the one or more instructions 124.

The term "machine readable medium" may include any medium that is capable of storing, encoding, or carrying instructions for execution by the device 100 and that cause the device 100 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium includes a machine readable medium with a plurality of particles having resting mass. Specific examples of massed machine readable media may include: non-volatile memory, such as semiconductor memory devices (e.g., Electrically Programmable Read-Only Memory (EPROM), or Electrically Erasable Programmable Read-Only Memory (EEPROM)) and flash memory devices; magnetic disks, such as internal hard disks and removable disks; magnetooptical disks; and CD-ROM and DVD-ROM disks.

The instructions 124 may further be transmitted or received over a communications network 126 using a transmission medium via the network interface device/transceiver 120 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), Plain Old Telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15 family of standards, and peer-to-peer (P2P) networks, among others. In an example, the network interface device/transceiver 120 may include one or more physical jacks (e.g., Ethernet, coaxial, or phone jacks) or one or more antennas to connect to the communications network 126. In an example, the network interface device/transceiver 120 may include a plurality of antennas to wirelessly communicate using at least one of single-input multiple-output (SIMO), multiple-input multiple-output (MIMO), or multiple-input single output (MISO) techniques. The term "transmission medium" shall be taken to include any intangible medium that is capable of storing, encoding or carrying instructions for execution by the device 100, and includes digital or analog communications signals or other intangible media to facilitate communication of such software.

Figure 4:
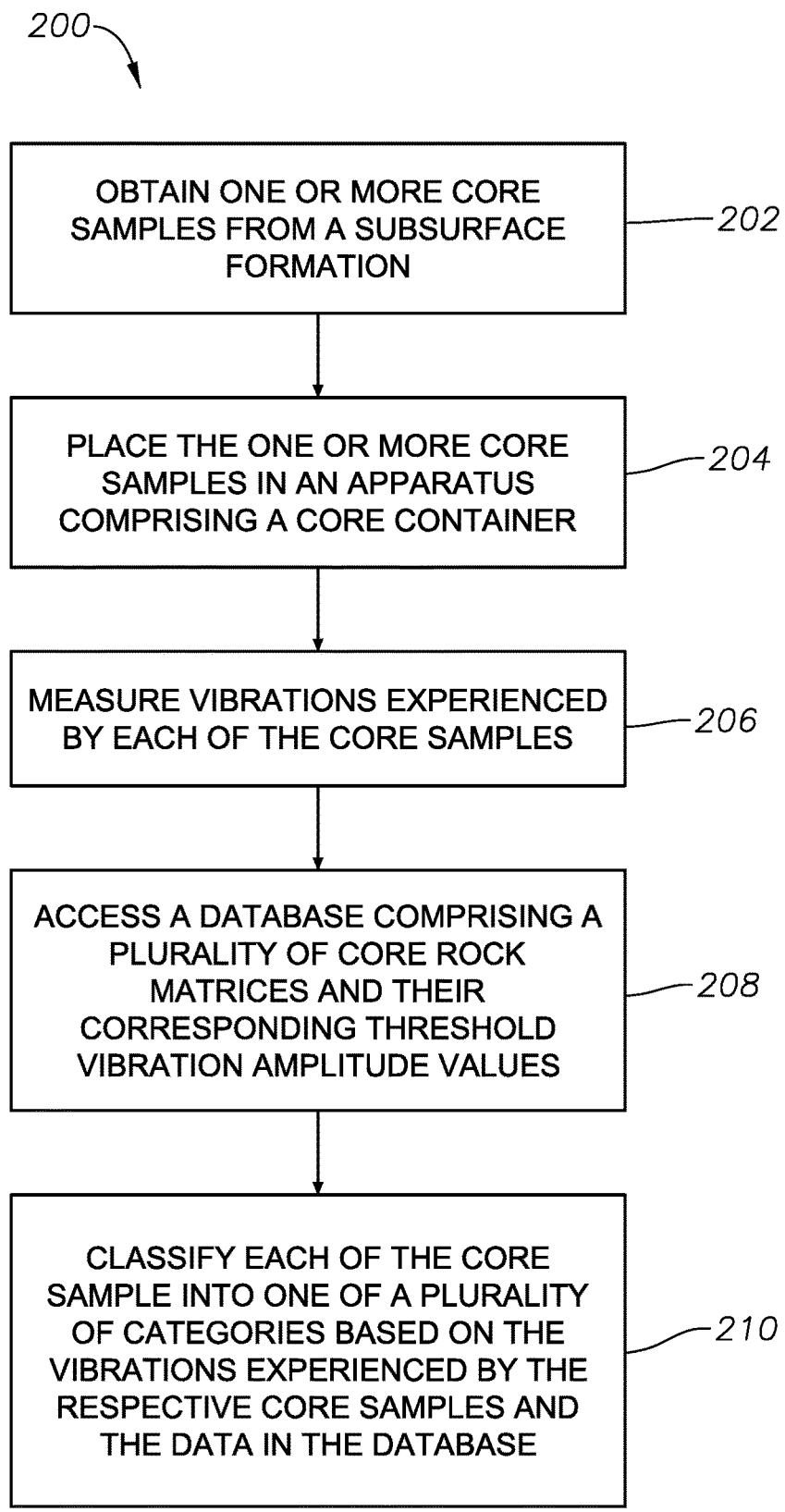
FIG. 4 illustrates example steps in a method for monitoring health and integrity of core samples, according to one or more example embodiments of the present disclosure.

FIG. 4 illustrates example steps in a method 200 for monitoring health and integrity of core samples, according to one or more example embodiments of the present disclosure. The method includes, at step 202, obtaining one or more core samples from a subsurface formation. The method includes, at step 204, placing the one or more core samples in an apparatus including a core container. The core container may include a body portion having a plurality of chambers to accommodate a plurality of samples, and a lid portion configured to fully cover the body portion. The method may further include, at step 206, measuring, by one or more vibration sensing devices, vibration experienced by each of the plurality of core samples. The method may also include, at step 208, accessing, by processor in the apparatus, a database including a plurality of core rock matrices and corresponding threshold vibration amplitude values. The method may also include, at step 210, determining, for each of the core samples, a category from a plurality of categories based on the vibration experienced by the core sample and the threshold vibration amplitude value for the corresponding core rock matrix. The step of determining may also include classifying each of the core samples into a category based on the vibrations experienced by the respective core sample, and the threshold vibration amplitude for the specific core rock matrix to which the core sample belongs.

The Specification, which includes the Summary, Brief Description of the Drawings and the Detailed Description, and the appended Claims refer to particular features (including process or method steps) of the disclosure. Those of skill in the art understand that the invention includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this invention belongs unless defined otherwise.

As used in the Specification and appended Claims, the singular forms "a," "an," and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. The verb "couple" and its conjugated forms means to complete any type of required junction, including electrical, mechanical or fluid, to form a singular object from two or more previously non-joined objects. If a first device couples to a second device, the connection can occur either directly or through a common connector. "Optionally" and its various forms means that the subsequently described event or circumstance may or may not occur. The description includes instances where the event or circumstance occurs and instances where it does not occur.

While there have been shown, described and pointed out, fundamental novel features of the invention as applied to the exemplary embodiments thereof, it will be understood that various omissions and substitutions and changes in the form and details of devices illustrated, and in their operation, may be made by those skilled in the art without departing from the spirit of the invention. Moreover, it is expressly intended that all combinations of those elements and/or method operations, which perform substantially the same function in substantially the same way to achieve the same results, are within the scope of the disclosure. Moreover, it should be recognized that structures and/or elements and/or method operations shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

What is claimed is:

1. An apparatus for monitoring integrity of a core sample, the apparatus comprising:
    a core container comprising:
       a body portion having a plurality of chambers to accommodate a plurality of samples; and
       a lid portion configured to fully cover the body portion;
    one or more vibration sensing devices configured to measure vibration experienced by each of the plurality of core samples;
    one or more processors; and
    a computer readable medium comprising computer readable instructions that when executed by the processor, cause the processor to:
       access a database comprising a plurality of core rock matrices and corresponding threshold vibration amplitude values; and
       determine, for each of the core samples, a category from a plurality of categories based on the vibration experienced by the core sample and the threshold vibration amplitude value for the corresponding core rock matrix.

2. The apparatus according to claim 1, wherein each of the one or more vibration sensing devices further comprise an accelerometer configured to measure vibration experienced by the respective core sample.

3. The apparatus according to claim 2, wherein each of the one or more vibration sensing devices further comprise a three-axis gyro configured to measure rotation of the core samples around three axes: x, y, and z.

4. The apparatus according to claim 3, further comprising one or more high definition cameras to capture images and/or videos of the one or more core samples.

5. The apparatus according to claim 4, further comprising a wireless transmitter configured to transmit the vibration data, image data, or video data to a receiver.

6. The apparatus according to claim 5, wherein the wireless transmitter is wirelessly connected to the receiver via radio frequency, Bluetooth, Bluetooth low energy, ZigBee, Wi-Fi, 2G, 3G, 4G LTE, 5G, or other wireless communication technique.

7. The apparatus according to claim 5, further comprising a battery unit configured to provide power to the one or more vibration sensing devices, the one or more high definition cameras, and the wireless transmitter.

8. The apparatus according to claim 1, wherein the plurality of categories comprise a plurality of colors, each color indicative of an amount of damage to the core sample.

9. The apparatus according to claim 1, further comprising a plurality of shock dampening devices configured to reduce an amount of shock experienced by each of the core samples.

10. The apparatus according to claim 1, wherein the database is stored locally on the computer readable medium or remotely on a computer or server.

11. A method for monitoring integrity of a core sample, the method comprising:
    obtaining one or more core samples from a subsurface formation;
    placing the one or more core samples in an apparatus comprising a core container, the core container comprising:
       a body portion having a plurality of chambers to accommodate a plurality of samples; and
       a lid portion configured to fully cover the body portion; and
    measuring, by one or more vibration sensing devices, vibration experienced by each of the plurality of core samples;
    accessing, by a processor in the apparatus, a database comprising a plurality of core rock matrices and corresponding threshold vibration amplitude values; and
    determining, for each of the core samples, a category from a plurality of categories based on the vibration experienced by the core sample and the threshold vibration amplitude value for the corresponding core rock matrix.

12. The method according to claim 11, wherein each of the one or more vibration sensing devices further comprise an accelerometer configured to measure vibration experienced by the respective core sample.

13. The method according to claim 12, wherein each of the one or more vibration sensing devices further comprise a three-axis gyro configured to measure rotation of the core samples around three axes: x, y, and z.

14. The method according to claim 13, further comprising capturing, by one or more high definition cameras, images and/or videos of the one or more core samples.

15. The method according to claim 14, further comprising transmitting, by a wireless transmitter, the vibration data, image data, or video data to a receiver.

16. The method according to claim 15, further comprising providing a battery unit to provide power to the one or more vibration sensing devices, the one or more high definition cameras, and the wireless transmitter.

17. The method according to claim 11, wherein the plurality of categories comprise a plurality of colors, each color indicative of an amount of damage to the core sample.

18. The method according to claim 11, further comprising providing a plurality of shock dampening devices to reduce an amount of shock experienced by each of the core samples.

* * * * *